United States Patent
Parramon et al.

(10) Patent No.: US 7,209,792 B1
(45) Date of Patent: Apr. 24, 2007

(54) RF-ENERGY MODULATION SYSTEM THROUGH DYNAMIC COIL DETUNING

(75) Inventors: Jordi Parramon, Valencia, CA (US); Goran N. Marnfeldt, Valencia, CA (US)

(73) Assignee: Advanced Bionics Corporation, Valencia, CA (US)

( * ) Notice: Subject to any disclaimer, the term of this patent is extended or adjusted under 35 U.S.C. 154(b) by 587 days.

(21) Appl. No.: 10/133,766

(22) Filed: Apr. 26, 2002

Related U.S. Application Data

(60) Provisional application No. 60/293,302, filed on May 24, 2001.

(51) Int. Cl.
  *A61N 1/08* (2006.01)
(52) U.S. Cl. .................. 607/120; 343/860; 333/173
(58) Field of Classification Search .......... 607/2, 607/4, 5, 9, 10, 30–33, 60–62, 48, 49; 323/222; 343/860, 861; 333/17.3, 32
See application file for complete search history.

(56) References Cited

U.S. PATENT DOCUMENTS

| | | | |
|---|---|---|---|
| 4,524,774 A | 6/1985 | Hildebrandt | |
| 5,193,539 A * | 3/1993 | Schulman et al. | 607/61 |
| 5,324,316 A | 6/1994 | Schulman et al. | |
| 5,358,514 A * | 10/1994 | Schulman et al. | 607/61 |
| 6,073,050 A | 6/2000 | Griffith | |
| 6,212,431 B1 | 4/2001 | Hahn et al. | |
| 6,214,032 B1 * | 4/2001 | Loeb et al. | 607/1 |
| 6,321,118 B1 | 11/2001 | Hahn | |
| 6,542,777 B1 | 4/2003 | Griffith et al. | |
| 6,553,263 B1 * | 4/2003 | Meadows et al. | 607/61 |
| 6,608,603 B2 * | 8/2003 | Alexopoulos et al. | 343/860 |
| 6,631,296 B1 | 10/2003 | Parramon et al. | |
| 6,804,561 B2 * | 10/2004 | Stover | 607/60 |

* cited by examiner

*Primary Examiner*—Robert E. Pezzuto
*Assistant Examiner*—Frances P. Oropeza
(74) *Attorney, Agent, or Firm*—Bryant R. Gold; Laura Bishop; Steven L. Nichols

(57) ABSTRACT

An RF-energy modulation system dynamically adjusts tuned receiving circuits within a plurality of slave devices, thereby regulating the level of power reception in each slave device. The slave devices receive power from a single master device, through coupling of a primary antenna in the master device with a secondary antenna in each slave device. The amount of the power received by each slave device is a function of the antenna separation distance, and is thus different at each slave device location. The RF-energy modulation system monitors the power requirements of the slave device within which the modulation system is included, and modulates the tuning of the secondary antenna to maintain the proper power reception level. Advantageously, such modulation controls the power reception by the slave device, versus dissipating energy already received by the slave device. In a preferred embodiment, the RF-energy modulation system controls the power received by a multiplicity of microstimulators implanted in a single patient.

17 Claims, 5 Drawing Sheets

RF-ENERGY MODULATION SYSTEM THROUGH DYNAMIC COIL DETUNING

The present application claims the benefit of U.S. Provisional Application Ser. No. 60/293,302, filed May 24, 2001, which application is incorporated herein by reference.

BACKGROUND OF THE INVENTION

The present invention relates to implantable medical devices and more particularly to an improvement to known methods for providing power from a single external device to a multiplicity of implantable microstimulators implanted within the same patient. Known implantable microstimulators receive power inductively from an external device. The improvement provided by the present invention dynamically adjusts the power reception of individual microstimulators to compensate for differences in the separation of each microstimulator from the external device.

Implantable microdevices have the potential to address a number of useful purposes. These purposes range from pain mitigation to Functional Electrical Stimulation (FES). Some of these applications require that a multiplicity of microdevices be implanted in a single patient. For example, paraplegics and quadriplegics often have muscles capable of functioning, but are paralyzed due to damage to nerves that carry impulses to the muscles. Additionally, individuals afflicted with neuro degenerative diseases such as polio and Amyotrophic Lateral Sclerosis (also known as ALS, or Lou Gehig's disease) may be similarly disabled. Functional Electrical Stimulation provides such individuals with use of their muscles by providing artificial stimulation pulses to the patient's muscles, which stimulation pulses result in a desired movement. However, in order to provide effective use of muscles, a number of microstimulators must stimulate various muscles in the arms or legs of the patient in a coordinated fashion.

Prosthetic devices have been used for some time to provide electrical stimulation to excite muscle, nerve or other tissue. Some of these devices have been large bulky systems providing electrical pulses through conductors extending through the skin. Disadvantageously, complications, including the possibility of infection, arise in the use of stimulators which have conductors extending through the skin.

Other smaller stimulators are implants which are controlled through high-frequency, modulated, RF telemetry signals. An FES system using telemetry signals is set forth in U.S. Pat. No. 4,524,774, issued Jun. 25, 1985 for "Apparatus and Method for the Stimulation of a Human Muscle." The '774 patent teaches a source of electrical energy, modulated by desired control information, to selectively control and drive numerous, small stimulators, disposed at various locations within the body. Thus, for example, a desired progressive muscular stimulation may be achieved through the successive or simultaneous stimulation of numerous stimulators, directed by a single source of information and energy outside the body.

Many difficulties arise in designing RF powered implantable stimulators which are small in size, and are also capable of receiving sufficient energy and control information to satisfactorily operate without direct connection. A design for a small functionally suitable stimulator, a microstimulator, is taught is U.S. Pat. No. 5,324,316 issued Jun. 28, 1994 for "Implantable Microstimulator," incorporated herein by reference. The '316 patent teaches all the elements required for successful construction and operation of a microstimulator. The microstimulator is capable of receiving and storing sufficient energy to provide the desired stimulating pulses, and also is able to respond to received control information specifying pulse duration, amplitude and shape. The microstimulator of the '316 patent can also be easily implanted, such as by expulsion through a large gauge hypodermic needle.

A large number of microstimulators may be required to stimulate different nerves or muscles in a coordinated manner to achieve a desired motion, or to treat some other medical condition. Known microdevices may either be continuously powered through an RF signal, or may contain a battery that is periodically recharged through an RF signal. In either case, power is provided inductively from an external device to the implantable microdevices. Further, it is desirable to utilize a single external device to provide power to all of the microdevices in a single patient. When using such a single external device, the distance between the external device and the implantable microdevices may vary greatly.

For distances much shorter than the wavelength of the RF signal (e.g., a 3 MHz signal has a wavelength of 100 meter), the magnetic field decays as $1/r^3$. The energy received by the microdevice is proportional to the square of the magnetic field strength. Therefore, the energy received by a microdevice, with separation r from the external device, attenuates as $1/r^6$. As a result, small variations in the separation of individual microdevices from the external device, result in very large variations in the energy received by the microdevices. For example, a first microdevice located half the distance from the external device as a second microdevice receives sixty four times more energy than the second microdevice. The microdevices proximal to the external device may have difficulty dissipating the energy they receive, and overheat as a result.

Known microdevices have a surface area of about 2 cm$^2$. Power dissipation from such a device is about 40 mW/cm$^2$ for a 2 degree centigrade temperature rise, resulting in a capability to safely dissipate 80 mW of power with a 2 degree centigrade temperature increase. A typical microdevice requires about 6 mW of power to charge. Thus, if the ratio of separation of individual microdevices from the external device is two, and the microdevice farther from the external device receives 6 mW, the microdevice nearer the external device receives 384 mW of total power, and therefore 378 mW of excess power. The requirement to dissipate the excess power results in a dangerous increase in the temperature of the microdevice and unacceptable heating of adjacent tissue.

What is therefore needed is a method for limiting the power received by microdevices that are near the external device.

SUMMARY OF THE INVENTION

The present invention addresses the above and other needs by providing power reception circuits including control circuits that dynamically adjust the power reception circuits of a plurality of individual slave devices (e.g., implantable microdevices implanted in a single patient), and thereby maintain an acceptable level of power reception in each slave device. A master device provides the RF-energy to the slave devices through inductive coupling. The control circuit in each slave device monitors the power reception of the slave device they are included in, and detunes the power reception circuit within the slave device, when necessary, to limit the power reception level of the slave device.

In accordance with one aspect of the invention, there is provided a detuning circuit corresponding to each power reception circuit of each slave device. The slave devices receive power from a single master device through inductive coupling of a primary coil in the master device with secondary coils in the slave devices. The power transferred through the inductive coupling is proportional to the coil separation distance to the sixth power. Thus, the slave devices near the master device receive significantly more power than slave devices farther from the master device, and may over heat. The energy reception is also related to how well the power reception circuit is tuned to the resonant frequency of the primary coil. The detuning circuit monitors the power received by the slave devices, and detunes the power reception circuit from the primary coil when the power level exceeds a threshold, thereby reducing the energy received by the slave devices.

It is a feature of the invention that the detuning circuit reduces the coupling between the primary coil in the master device and the power reception circuit in the slave device. Known master devices are battery powered, and the life of the battery is an important feature of such master device. The master device provides power to implantable slave devices over an inductive link, and the power drawn from the master device by such inductive link is related to the magnetic coupling between the primary and secondary coils and the matching factor of the transmitting and receiving circuits. Advantageously, limiting power received by the slave devices, by reducing the matching factor between the master device and the slave devices, reduces the power drawn from the master device, and extends battery life.

It is an additional feature of the present invention to provide a controlled range of voltages to battery charging circuits within the implantable slave devices. The battery charging circuit is adapted to provide the correct power to the battery for effective charging. However, when the voltage provided to the charging circuit is higher than the battery charging voltage, power is dissipated within the charging circuit to achieve the necessary voltage reduction. Such power dissipation results in the generation of heat within the charging circuit, and a reduction of the life of the charging circuit. By controlling the range of voltage provided to the charging circuit, the present invention reduces the power dissipated within the charging circuit, and extends the life of the charging circuit.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
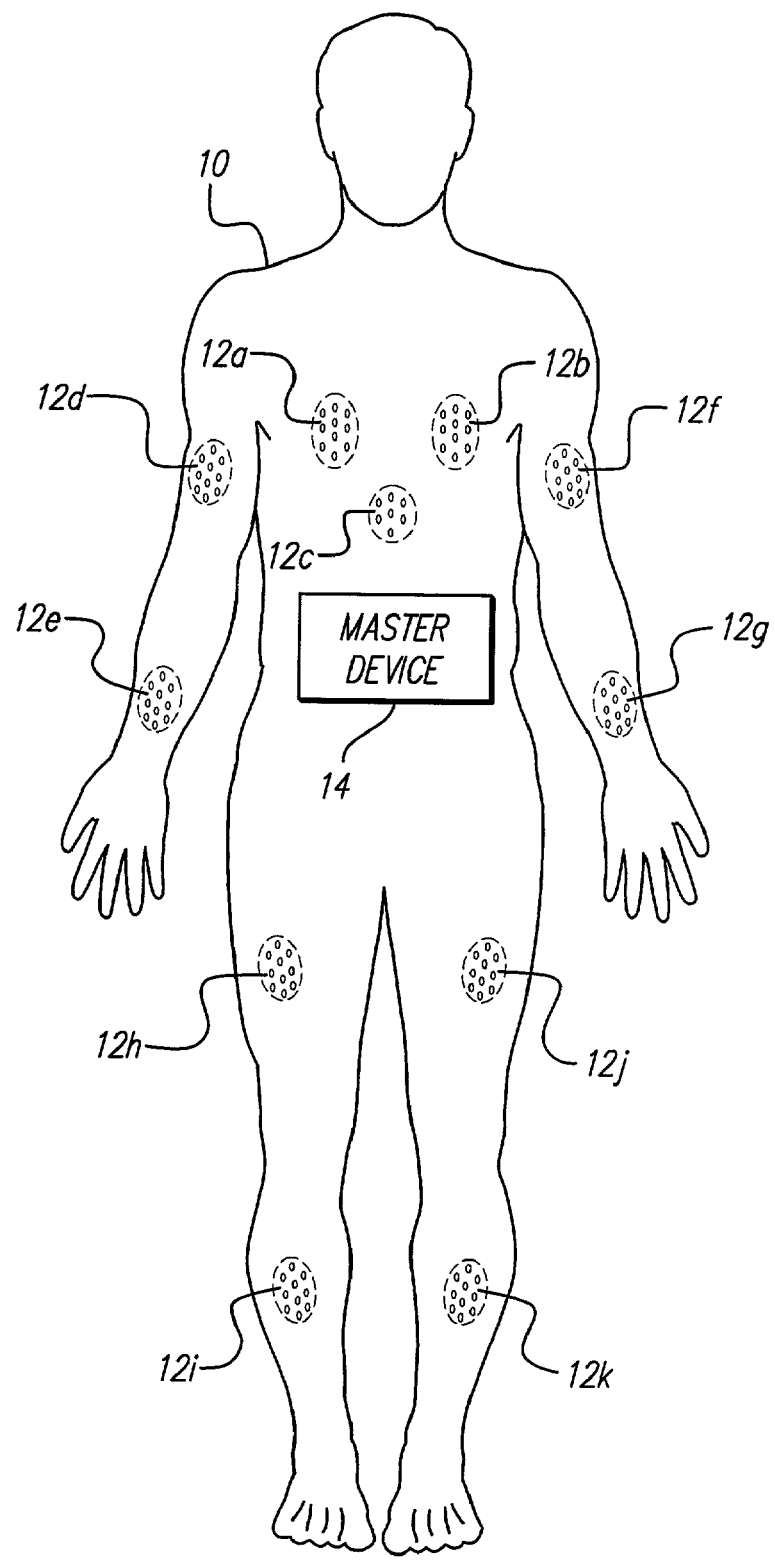
FIG. 1 shows a master device and various muscle groups of a patient, which muscle groups may be stimulation sites.

A Functional Electrical Stimulation (FES) system generates electrical signals to stimulate nerves and muscles to provide movement for paraplegics, quadriplegics, and other individuals with a neural lesion, a neuro degenerative disease, or other physical condition depriving the patient of the use of the muscles. Similarly, heart or lung muscles may be stimulated to provide the appropriate blood flow and oxygen for various activities, and various sensors may be implanted to monitor body functions. A master device 14 of an FES system centrally carried on a patient 10 is shown in FIG. 1. The master device 14 includes a primary antenna to transmit power and control signals to secondary antennas in a multiplicity of slave devices. In an FES system, the slave devices typically comprise slave devices implanted in various muscle groups including lungs 12$a$, 12$b$, heart 12C, arm muscles 12$d$–12$g$, and leg muscles 12$h$–2$k$. As can be seen from FIG. 1, the distances, separating the master device 14 from slave devices implanted in various muscles, may vary greatly in a single patient.

Figure 2:
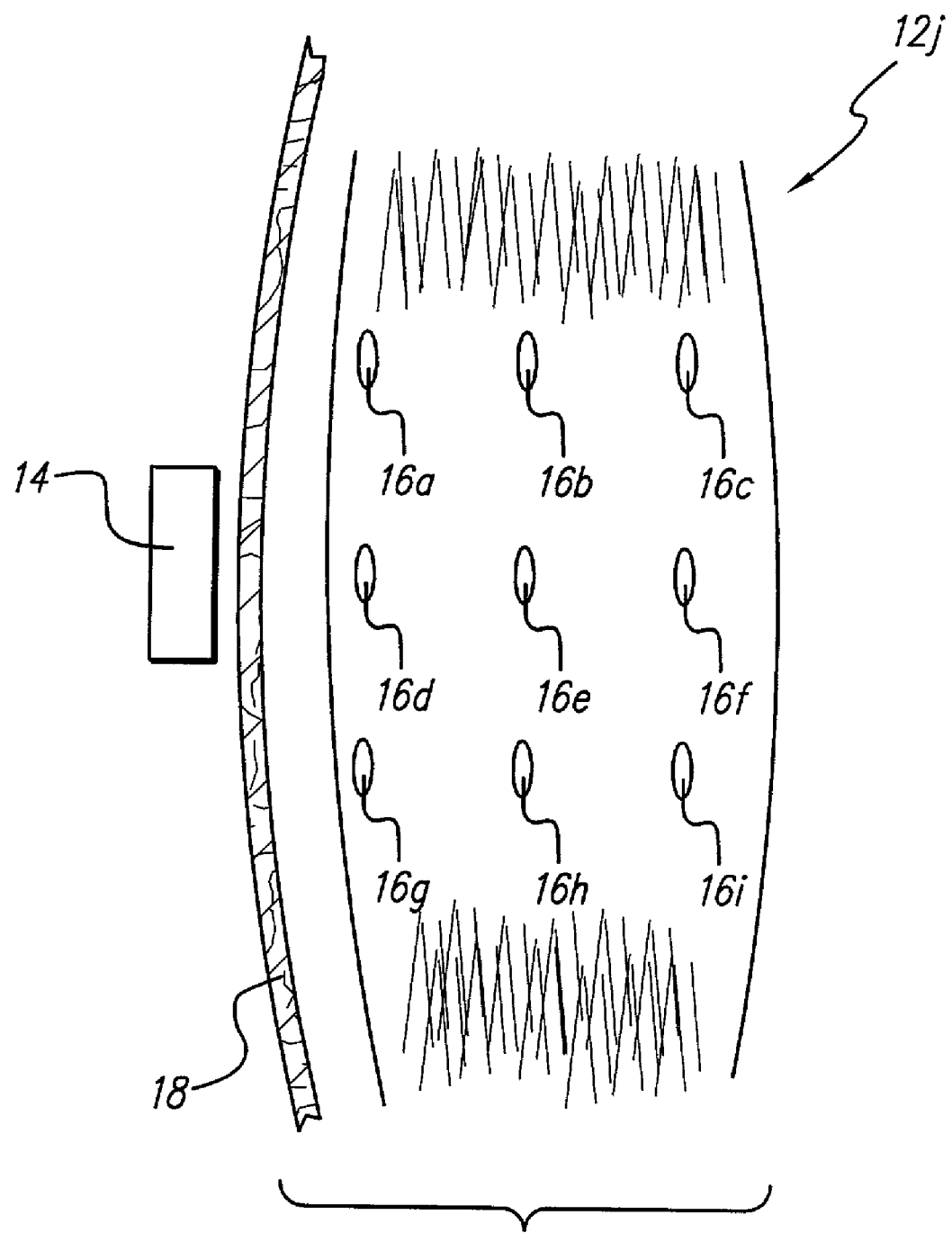
FIG. 2 depicts a group of microstimulators implanted in a single muscle and a master device residing outside the skin of the patient.

A view of slave devices 16$a$–16$i$ implanted in the leg muscle 12$j$ is shown in FIG. 2. The master device 14 is separated from slave devices 16$a$–16$i$ by the patient's skin 18. U.S. Pat. No. 5,324,316 issued Jun. 28, 1994, for "Implantable Microstimulator," incorporated by reference above, teaches the elements required for successful construction and operation of a microstimulator, which may serve as a slave device. A slave device according to the '316 patent advantageously may be implanted through a large gauge needle, thus providing a minimally invasive implant procedure.

As is evident in both FIGS. 1 and 2, the separation of individual slave devices 16$a$–16$i$ from master device 14 may vary greatly. Known implantable slave devices receive power inductively from an external device, such as the master device 14, through a magnetic field. The primary antenna in the master device 14 thus comprises a primary coil, and the secondary antenna in each slave device thus comprises a secondary coil. The magnetic field received by a slave device, with separation distance r from the master device 14, decays as $1/r^3$. The power received by the slave device is proportional to the square of the magnetic field strength, and as a result the power decays as $1/r^6$. Therefore, a first slave device half the distance from the master device 14 as a second slave device, receives about 64 times the power the second slave device receives.

Figure 3:
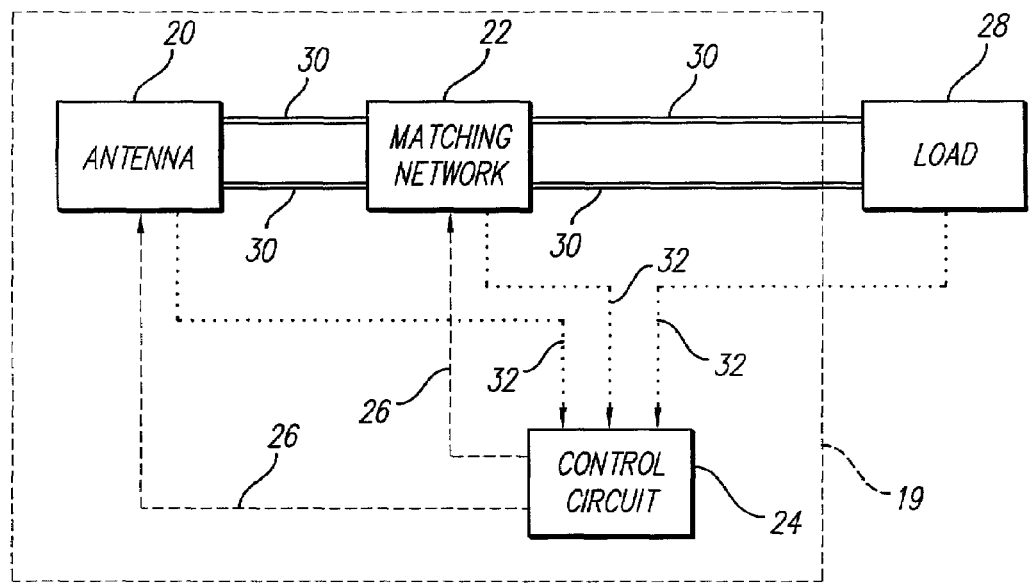
FIG. 3 functionally depicts a power reception circuit and load, which circuit is retunably detunable according to the present invention.

A generalized power reception circuit 19 is shown connected to a load 28 in FIG. 3. The power reception circuit 19 may be included in each slave device 16a–16i. An antenna 20 may be any device that receives energy. The antenna 20 is electrically connected by at least one conductor 30 to a matching network 22 (in the case of a single conductor 30, the antenna 20 and matching network 22 may also be connected to a common ground). The matching network 22 electrically cooperates with the antenna 20 to match (i.e., to tune, or to increase the matching factor), the power reception circuit 19 to the power signals received by the antenna 20. The load 28 is electrically connected by at least one conductor 30 to the power reception circuit 19 (in the case of a single conductor 30, the load 28 and the power reception circuit 19 may also be connected to a common ground). Monitoring signal paths 32 connect the antenna 20, the matching network 22, and/or the load 28 to a control circuit 24. The control circuit 24 may receive monitoring signals from the antenna 20, the matching network 22, or the load 28, or any combination of the antenna 20, the matching network 22, or the load 28, over the signal paths 32. The control circuit 24 preferably monitors the voltage at a circuit node, but could monitor a current, energy level, or temperature of a circuit component, and these and other measures of power reception are intended to come within the scope of the present invention. Control signals 26 are sent from the control circuit 24 to the antenna 20 or the matching network 22, or both the antenna 20 and the matching network 22, to modify the electrical characteristics (e.g., resonate frequency) of the power reception circuit 19, thus controlling the amount of power received by the power reception circuit 19 from the master device 14. In a first example, when the power reception level measured by the control circuit 24 exceeds a first limit, the control circuit 24 uses the control signals 26 to reduce the power reception level (i.e., detune the power reception circuit 19), and when the power reception level drops below a second limit, the control circuit 24 uses the control signals 26 to increase the power reception level (i.e., retune the power reception circuit 19). The power reception circuit 19 may thus be retunably detuned. In a second example, a control circuit continuously adjusts the power reception circuit 19 to substantially maintain (i.e., maintain within a range) a target power reception level. Other methods of controlling the power reception level will be apparent to those skilled in the art and are intended to come within the scope of the present invention.

Figure 4A:
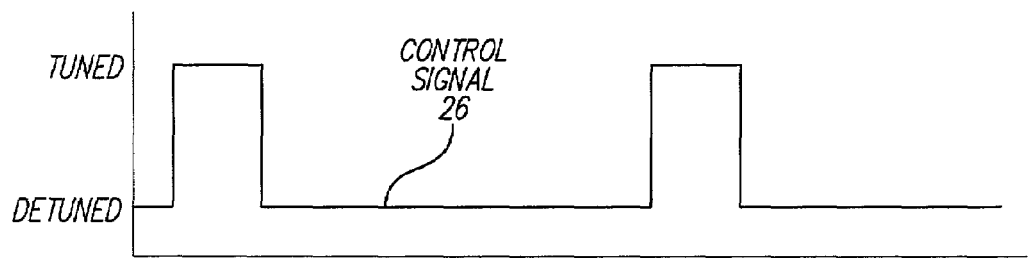
FIG. 4A plots a typical control signal for modulating the tuning and detuning of the power reception circuit.
Figure 4B:
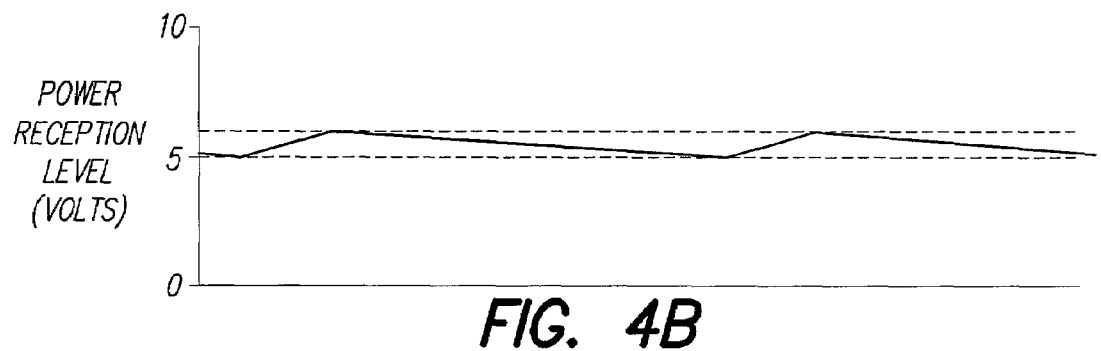
FIG. 4B plots a typical voltage level resulting from the modulation depicted in FIG. 4A.

A plot of one example of the control signal 26 of the power reception circuit 19 is shown in FIG. 4A, and a plot of the resulting power reception is shown in FIG. 4B. When power is first received by the slave device, the power reception level begins to rise. The rate of rise depends on the strength of the magnetic field in the vicinity of the slave device. The control circuit 24 monitors the power being received, and when the power level reaches or exceeds a predetermined threshold, for example, a high voltage threshold Vh (preferable 6.0 volts), the control circuit 24 detunes the power reception circuit. When the power reception circuit is detuned, the secondary antenna is no longer tuned to the primary antenna, the magnetic coupling between the primary antenna and the secondary antenna is reduced, and the current induced in the secondary antenna is reduced. The reduction in current results in the power reception dropping. The control circuit 24 continues to monitor the power reception, and when the power reception drops to or below a predetermined minimum threshold, for example a low voltage threshold Vm (preferable 5.0 volts), the control circuit 24 retunes the power reception circuit, and power reception level begins to rise again.

Figure 5:
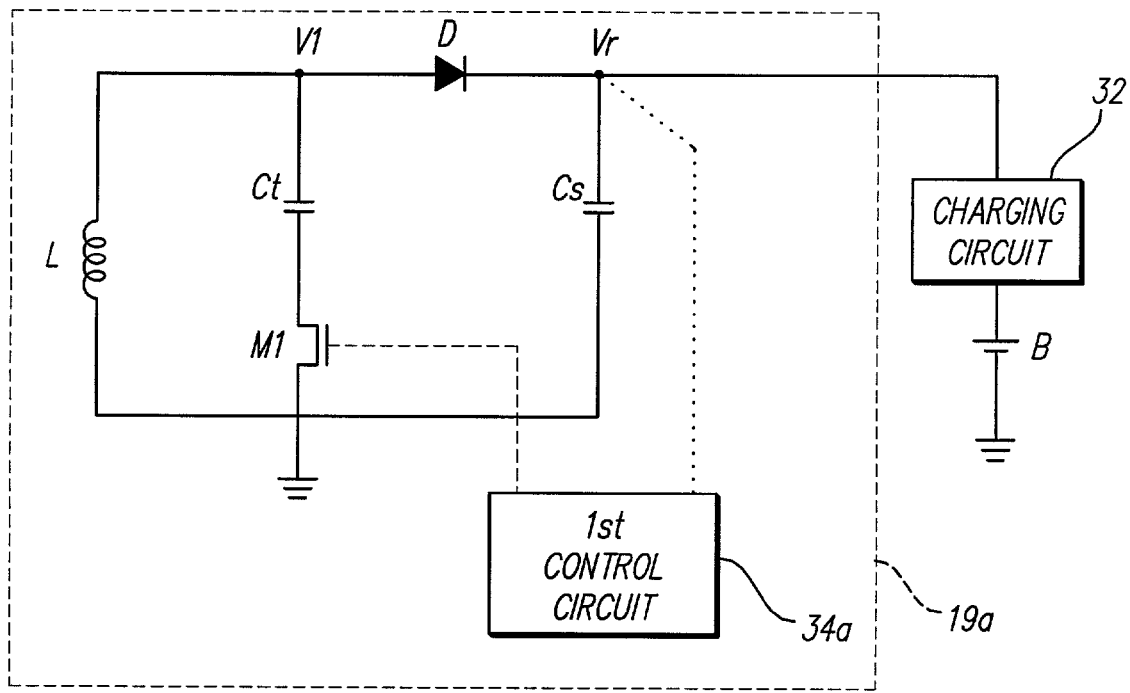
FIG. 5 schematically depicts a first embodiment of a power reception circuit according to the present invention.

A first power reception circuit 19a is shown schematically in FIG. 5. Such circuit may be included in each slave device. The antenna (i.e., secondary coil) of the power reception circuit 19a comprises an inductor L. The inductor L is electrically connected between ground and a first voltage node V1. A tuning capacitor Ct and first switch M1 are electrically connected in series between the node V1 and ground. A diode D is electrically connected between the node V1 and a rectified voltage node Vr. A storage capacitor Cs is electrically connected between the node Vr and ground. A load in the form of a charging circuit 32 and a battery B are electrically connected in series between the node Vr and ground. A first control circuit 34a monitors the voltage at the node Vr, and controls the switch M1. The power signals are represented by solid lines, the monitoring signal is represented by a dotted line, and the control signal is represented by a dashed line. When the switch M1 is closed, the capacitor Ct is electrically connected to the inductor L, thereby tuning the power reception circuit 19a to the primary antenna for efficient reception of the power transmitted by the master device 14. When the switch M1 is opened, the capacitor Ct is electrically disconnected to the inductor L, thereby detuning the power reception circuit 19a from the primary antenna and attenuating reception of power transmitted by the master device 14. The control circuit 34a includes a first reference voltage and a second reference voltage. When the voltage at the node Vr exceeds the first reference voltage, the control circuit 34a opens the switch M1. When the voltage at the node Vr is below the second reference voltage, the control circuit 34a closes the switch M1.

Figure 6:
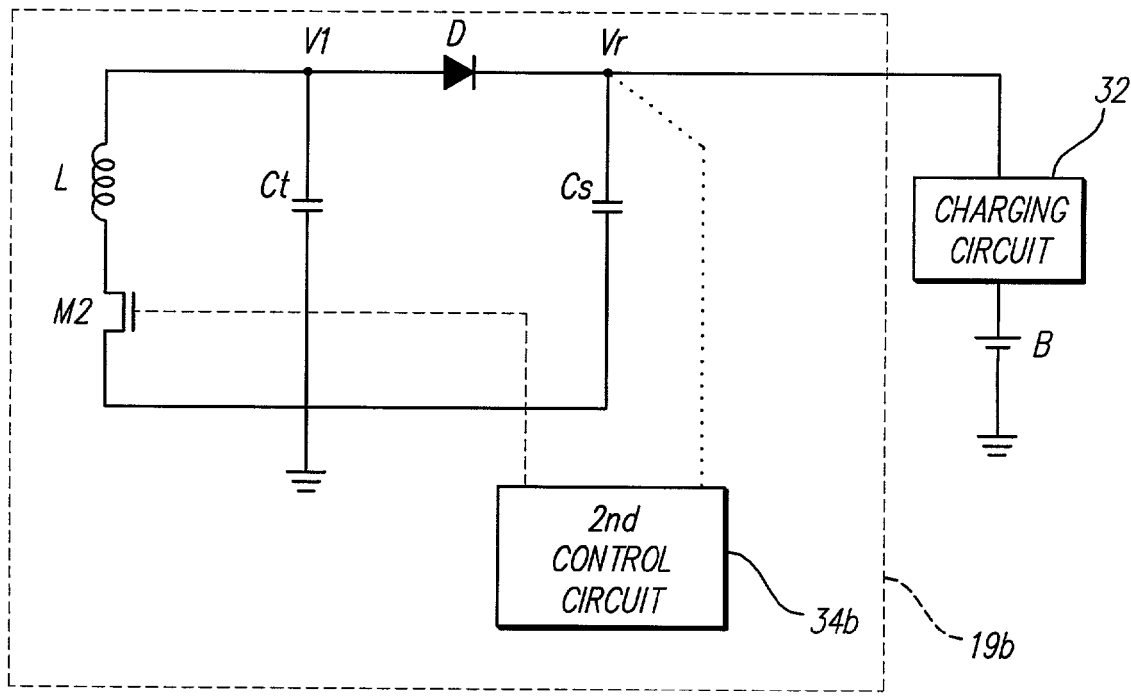
FIG. 6 schematically depicts a second embodiment of a power reception circuit according to the present invention.

A second power reception circuit 19b is shown schematically in FIG. 6. Such circuit may be included in each slave device. The antenna (i.e., secondary coil) of the power reception circuit 19b comprises an inductor L. The inductor L and a second switch M2 are electrically connected in series between ground and a first voltage node V1. A tuning capacitor Ct is electrically connected between the node V1 and ground. A diode D is electrically connected between the node V1 and a rectified voltage node Vr. A storage capacitor Cs is electrically connected between the node Vr and ground. A load in the form of a charging circuit 32 and a battery B are electrically connected in series between the node Vr and ground. A second control circuit 34b monitors the voltage at the node Vr, and controls the switch M2. The power signals are represented by solid lines, the monitoring signal is represented by a dotted line, and the control signal is represented by a dashed line. When the switch M2 is closed, the inductor L is electrically connected to ground to complete a tuned antenna circuit, thereby tuning the power reception circuit 19b to the primary antenna for efficient reception of the power transmitted by the master device 14. When the switch M1 is opened, the inductor L is in an open circuit, thereby detuning the power reception circuit 19b from the primary antenna and attenuating reception of the power transmitted by the master device 14. The control circuit 34B controls the switch M2 in the same manner that the control circuit 34a controls the switch M1.

Figure 7:
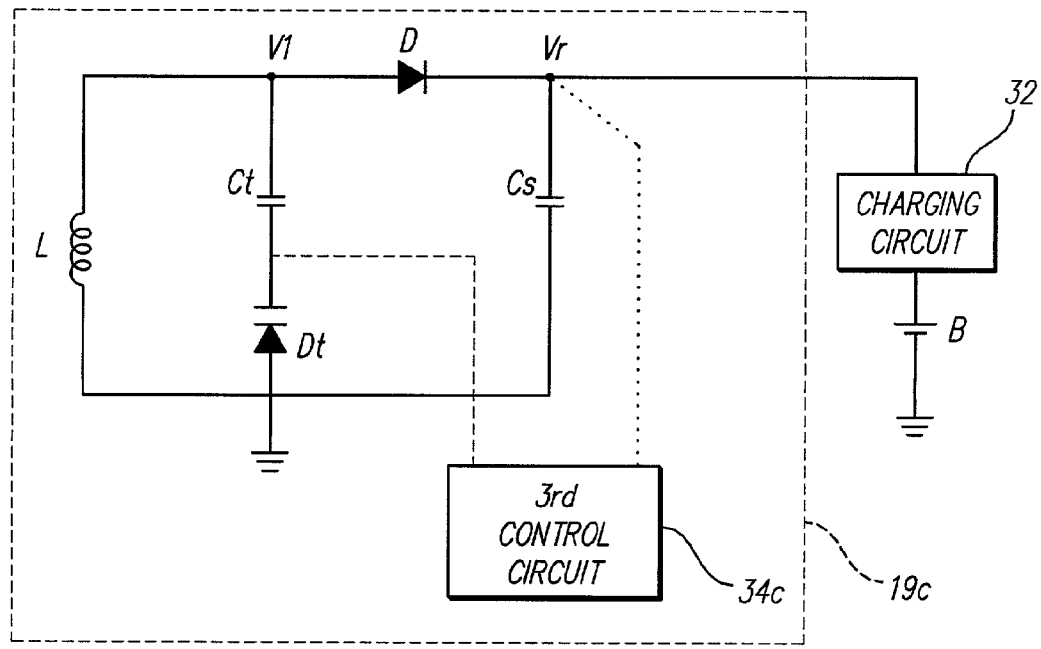
FIG. 7 schematically depicts a third embodiment of a power reception circuit according to the present invention.

A third power reception circuit 19c is shown schematically in FIG. 7. Such circuit may be included in each slave device. The antenna (i.e., secondary coil) of the power reception circuit 19c comprises an inductor L. The inductor L is electrically connected between ground and a first voltage node V1. A tuning capacitor Ct is electrically connected in series with a varactor Dt, between the node V1 and ground. A diode D is electrically connected between the node V1 and a rectified voltage node Vr. A storage capacitor Cs is electrically connected between the node Vr and ground. A load in the form of a charging circuit 32 and a battery B are electrically connected in series between the node Vr and ground. A third control circuit 34c monitors the voltage at the node Vr, and controls the variable capacitance of the varactor Dt, and thereby controls the total capacitance between the node V1 and ground. The power signals are represented by solid lines, the monitoring signal is represented by a dotted line, and the control signal is represented by a dashed line. When the voltage at the node Vr drifts away from a third reference voltage, the control circuit 34c adjusts the variable capacitance of the varactor Dt to drive the voltage at the node Vr toward the third reference voltage.

Figure 8:
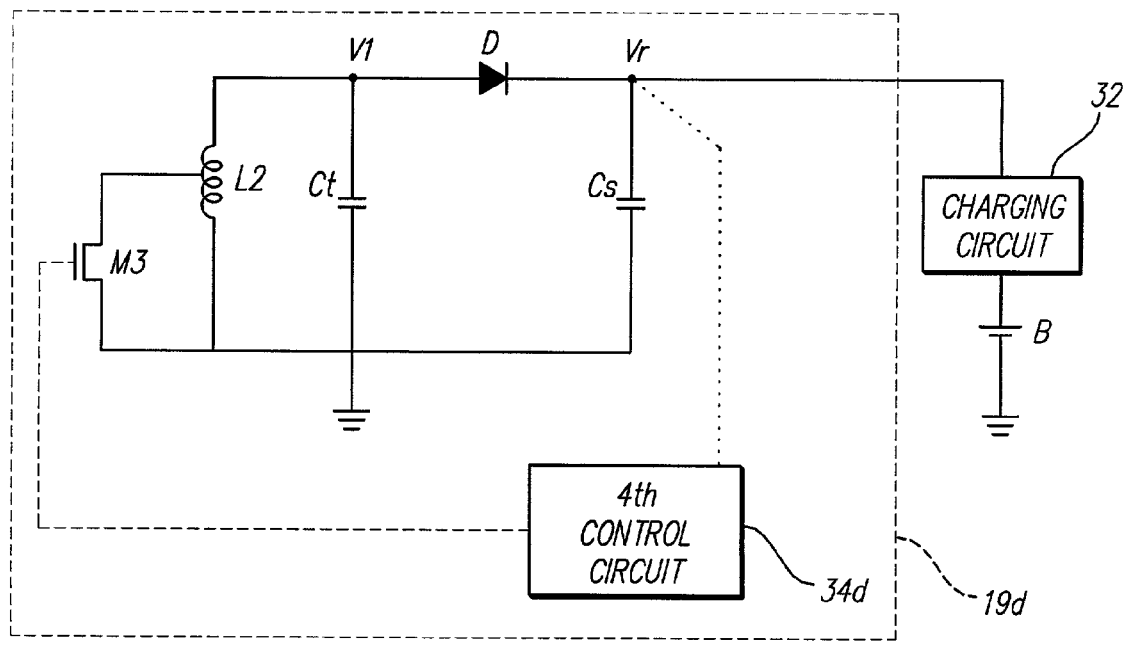
FIG. 8 schematically depicts a fourth embodiment of a power reception circuit according to the present invention.

A fourth power reception circuit 19d is shown schematically in FIG. 8. Such circuit may be included in each slave device. The antenna (i.e., secondary coil) of the power reception circuit 19d comprises a second inductor L2. The inductor L2 is electrically connected between ground and a first voltage node V1. The inductor L2 includes a tap point substantially centered on the windings of the inductor L2. A third switch M3 is electrically connected between the tap point and ground. A tuning capacitor Ct is electrically connected between the node V1 and ground. A diode D is electrically connected between the node V1 and a rectified voltage node Vr. A storage capacitor Cs is electrically connected between the node Vr and ground. A load in the form of a charging circuit 32 and a battery B are electrically connected in series between the node Vr and ground. A fourth control circuit 34d monitors the voltage at the node Vr, and controls the switch M3. The power signals are represented by solid lines, the monitoring signal is represented by a dotted line, and the control signal is represented by a dashed line. When the voltage at the node Vr exceeds the first reference voltage, the switch M3 is closed, and the tap point on the inductor L2 is electrically connected to ground, thereby detuning the power reception circuit 19d from the primary antenna and attenuating reception of the power transmitted by the master device 14. When the voltage at the node Vr drops below a second reference voltage, the switch M3 is opened, and the tap point of the inductor L2 is electrically disconnected from ground, thereby tuning the power reception circuit 19d to the primary antenna for efficient reception of the power transmitted by the master device 14. Those skilled in the art will recognize that a third inductor L3 could be substituted for the inductor L2, wherein the circuit is tunned when the switch M3 is closed, and detuned when the switch M3 is open. Similarly, the tap point could be moved away from the center of the inductor L2 or L3.

The power reception circuits described above in FIGS. 5–8 represent exemplary embodiments, and any one of these circuits could be used to practice the invention. Various equivalent circuits exist also. In many applications, the power received by the slave device is used to charge a battery. In other applications, the power may be used to charge a capacitor or other energy storage device, or used directly to perform a useful task. These variations are intended to come within the scope of the present invention. Further, in the embodiments described herein, a single diode was used as a rectifying element. Those skilled in the art will recognize that other rectifying elements, such as a diode bridge, synchronous switch, etc. may be used, and are intended to come within the scope of the present invention. While the examples in FIGS. 5, 6, 7, and 8, show circuit elements connected to a common ground, the circuit elements may also be connected to any common reference potential. Similarly, power may be transferred between a master device and a slave device using methods other than inductive coupling. Thus, any method for controlling power reception by detuning (i.e., reducing the matching factor) a secondary antenna circuit from a primary antenna circuit, regardless of variations in the power reception circuit or method of power transmission, is intended to come within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A power reception circuit for regulating power received from a master device, comprising:
    a secondary antenna for receiving power and outputting a current;
    a matching network configured to electrically cooperate with the secondary antenna to tune the power reception circuit to efficiently receive power from the master device; and
    a control circuit connected to said antenna and said matching network, wherein said control circuit comprises either a current or temperature monitor and selectively tunes and detunes said power reception circuit in response to the current output by the secondary antenna or a temperature.

2. The circuit of claim 1 wherein the power reception circuit resides in a slave device, and wherein the master device provides power to the slave device.

3. The circuit of claim 2 wherein the slave device includes an energy storage device, and wherein the power recharges the energy storage device.

4. The circuit of claim 3 wherein the energy storage device comprises a battery.

5. The system of claim 1 wherein the master device includes a primary coil, and wherein the secondary antenna comprises a secondary coil, and wherein the power is inductively transmitted from the primary coil to the secondary coil.

6. The system of claim 1 wherein the master device is a master controller of an implantable medical device system, and wherein the power reception circuit resides in each of a plurality of implantable microdevices.

7. The system of claim 6 wherein the implantable microdevices comprise implantable microstimulators.

8. The system of claim 6 wherein the implantable microdevices comprise implantable microsensors.

9. The system of claim 6 wherein the implantable microdevices comprise implantable microsensors and implantable microstimulators.

10. A power reception circuit for regulating power received from a master device, comprising:
    a secondary antenna;
    a matching network connected with the secondary antenna and configured to selectively tune the power reception circuit to efficiently receive power from the master device; and
    means for controlling the power reception circuit to retunably detune the power reception circuit;
    wherein the means for controlling the power reception circuit comprise at least one of a current or temperature monitor and are configured to detune the power reception circuit when the current or temperature produced by the slave device exceeds a first threshold, and to retune the power reception circuit when the current or temperature produced by the slave device is less than a second threshold.

11. A power reception circuit for an implantable device, comprising:
an antenna;
a first node V1, wherein the antenna is electrically connected between the node V1 and a reference potential;
a tuning element connected between the node V1 and the reference potential;
a detuning means configured to selectively detune the power reception circuit; and
a control circuit comprising at least one of a current or temperature monitor, wherein said control circuit is configured to selectively control the detuning means in response to either a current or temperature produced by the implantable device so as to maintain power received by the power reception circuit between a first power reception value and a second power reception value.

12. The circuit of claim 11 further including:
a rectifying element; and
a second node Vr electrically connected to the node V1, wherein the rectifying element is electrically connected between the node V1 and the node Vr, wherein the rectifying element is configured to allow current to flow from the node V1 to the node Vr, and the rectifying element is configured to prevent current from flowing from the node Vr to the node V1.

13. The circuit of claim 12 wherein:
the antenna is a secondary coil of an inductive powering system; and
the rectifying element comprises a diode.

14. The circuit of claim 12 wherein the power reception circuit is configured to provide power to a charging circuit and an energy storage device.

15. A method for controlling the amount of power transferred between a master device and a slave device, comprising:
transmitting power from a primary antenna in the master device to a secondary antenna in the slave device;
receiving the power with a power reception circuit comprising the secondary antenna;
monitoring either a temperature or a current produced by the power reception circuit; and
controlling the power reception circuit to maintain the temperature or current between a high threshold and a minimum threshold.

16. The method of claim 15 wherein transmitting power from the primary antenna in the master device to the secondary antenna in the second device comprises transmitting power from a primary coil in the master device to a secondary coil in the second device.

17. The method of claim 15 wherein controlling the power reception circuit further comprises selectively tuning and detuning the power reception circuit to maintain the temperature or current between a high threshold and a minimum threshold.

* * * * *